United States Patent [19]
Nielsen et al.

[11] Patent Number: 5,989,600
[45] Date of Patent: Nov. 23, 1999

[54] METHOD FOR IMPROVING THE SOLUBILITY OF VEGETABLE PROTEINS

[75] Inventors: Per Munk Nielsen; Inge Helmer Knap, both of Bagsværd, Denmark

[73] Assignee: Novo Nordisk A/S, Bagsvaerd, Denmark

[21] Appl. No.: 08/716,450

[22] PCT Filed: Apr. 20, 1995

[86] PCT No.: PCT/DK95/00166

§ 371 Date: Sep. 27, 1996

§ 102(e) Date: Sep. 27, 1996

[87] PCT Pub. No.: WO95/28850

PCT Pub. Date: Nov. 2, 1995

[30] Foreign Application Priority Data

Apr. 22, 1994 [DK] Denmark ................. 0470/94

[51] Int. Cl.⁶ ................. A23L 1/29; A23L 1/00; A23L 1/03
[52] U.S. Cl. ................. 426/52; 426/53; 426/54; 426/807; 424/442; 424/439; 424/94.2; 424/438; 435/183; 435/219
[58] Field of Search ................. 424/442, 439, 424/94.2, 438; 435/183, 219; 426/52, 53, 54, 807

[56] References Cited

U.S. PATENT DOCUMENTS

| | | | |
|---|---|---|---|
| 3,297,548 | 1/1967 | Ware et al. ................. | 195/66 |
| 3,966,971 | 6/1976 | Morehouse et al. ................. | 426/44 |
| 4,324,805 | 4/1982 | Olsen ................. | 426/46 |
| 4,914,029 | 4/1990 | Caransa ................. | 435/101 |
| 5,612,055 | 3/1997 | Bedford et al. ................. | 424/442 |
| 5,863,533 | 1/1999 | Van Gorcom ................. | 424/94.6 |

FOREIGN PATENT DOCUMENTS

| | | |
|---|---|---|
| 0 420 358 A1 | 9/1990 | European Pat. Off. . |
| 4-023958 | 1/1992 | Japan . |
| WO 92/07474 | 5/1992 | WIPO . |
| WO 92/15696 | 9/1992 | WIPO . |

OTHER PUBLICATIONS

Graf, E., Phytic Acid, chemistry & applications, 1986 by Pilatus Press, Minneapolis, MN., pp. 1–21.
Knuckles et al., Effect of Myo–inositol Phosphate Esters on in Vitro and in Vivo Digestion of Protein, Journal of Food Science, vol. 54, No. 5, 1989, pp. 1348–1350.
Han et al. J Agric Food Chem 36 (2) pp. 259–262, Feb. 1988.
Sigma Catalog, p. 857 P3304 and P3429, Jan. 1996.

*Primary Examiner*—Chris Eisenschenk
*Assistant Examiner*—Mary K Zeman
*Attorney, Agent, or Firm*—Steve T. Zelson, Esq.; Elias Lambiris, Esq.

[57] ABSTRACT

The present invention relates to a method for improving the solubility of vegetable proteins. More specifically, the invention relates to methods for the solubilization of proteins in vegetable protein sources, which methods comprise treating the vegetable protein source with an efficient amount of one or more phytase enzymes, and treating the vegetable protein source with an efficient amount of one or more proteolytic enzymes. In another aspect, the invention provides animal feed additives comprising a phytase and one or more proteolytic enzymes.

31 Claims, No Drawings

METHOD FOR IMPROVING THE SOLUBILITY OF VEGETABLE PROTEINS

CROSS-REFERENCE TO RELATED APPLICATIONS

This application is a 35 U.S.C. 371 national application of PCT/DK95/00166 filed Apr. 20, 1995, which is incorporated herein by reference.

TECHNICAL FIELD

The present invention relates to a method for improving the solubility of vegetable proteins. More specifically, the invention relates to methods for the solubilization of proteins in vegetable protein sources, which methods comprise treating the vegetable protein source with an efficient amount of one or more phytase enzymes, and treating the vegetable protein source with an efficient amount of one or more proteolytic enzymes. In another aspect the invention provides animal feed additives comprising a phytase and one or more proteolytic enzymes.

BACKGROUND ART

Protein is an essential nutritional factor for a.o. mammals and layers. Most livestock and many human beings get the necessary proteins from vegetable protein sources. Important vegetable protein sources are e.g. cereals, legumes and oilseed crops.

Hydrolyzed vegetable proteins, such as soy protein hydrolysates, find application as nutrients, e.g. as nutritional additives to foods and beverages. Hydrolyzed proteins are absorbed more easily than unhydrolysed protein, whey protein hydrolysates are considered having the highest nutritional value. Several methods for preparing protein hydrolysates are known and described in the literature, cf. e.g. U.S. Pat. No. 4,324,805 and WO 92/15696.

Essentially all food and feed substances originating from plants contain phytate and phytic acid as a storage phosphorus source [cf. review in E. Graf (ed.), *Phytic Acid, Chemistry and Applications*, Minneapolis, U.S.A., 1986]. About 75–78% of the phosphorus in cereals is bound as phytic acid. Phytate comprises 1–3% of all nuts, cereals, legumes, oil seeds, spores and pollen. Complex salts of phytic acid are termed phytin.

Phytic acid chelates minerals such as calcium, zinc, magnesium, and iron, thereby decreasing the bio-availability of nutritionally important minerals, and is generally considered an anti-nutritional factor. In vitro studies indicate that phytic acid inhibits the peptic digestion of some animal proteins, whereas the trypsin digestion was unaffected [cf. Knuckles et al., *Journal of Food Science*. 1989 54 1348–1350].

Phytases are enzymes which catalyze the conversion of phytate to inositol and inorganic phosphorus. Phytases have been obtained from e.g. Bacillus, Pseudomonas, Saccharomyces and Aspergillus.

In U.S. Pat. No. 3,297,548 it has been suggested to add microbial phytase to feedstuffs of monogastric animals in order to avoid supplementing the feed with inorganic phosphorus.

It has also been conceived that phytases may be used in the processing of soy. Thus EP-A-0 420 358 reports that soybean meal contains high levels of the anti-nutritional factor phytate which renders this protein source unsuitable for application in baby food, as well as in feed for fish, calves and other non-ruminants, since the phytate chelates essential minerals present therein.

In summary it has previously been suggested to use phytase enzymes either for exploiting the phosphorus bound in the phytate/phytic acid present in vegetable protein sources, or for exploiting the nutritionally important minerals bound in phytic acid complexes.

However, there is a need for improving the availability of the proteins present in vegetable sources, e.g. cereals, legumes and oilseed crops, since an increased availability leads to higher yields of protein hydrolyzing processes as well as nutritional benefits, i.e. improved protein utilization.

SUMMARY OF THE INVENTION

It has now been found that the solubility of proteins present in vegetable sources may be increased by treating the vegetable source with an efficient amount of a phytase enzyme. By addition of a phytase during a proteolytic process, higher degrees of hydrolysis and improved protein solubility are obtained, and yields are improved.

Accordingly, the present invention provides a method for solubilizing proteins in a vegetable protein source, which method comprises treating the vegetable protein source with an efficient amount of one or more phytase enzymes, and treating the vegetable protein source with an efficient amount of one or more proteolytic enzymes.

In another aspect, the invention provides an animal feed additive comprising a phytase and a proteolytic enzyme.

DETAILED DISCLOSURE OF THE INVENTION

Solubilization of Vegetable Proteins

The present invention provides a method for the solubilization of proteins in a vegetable protein source, thereby obtaining a protein hydrolysate. The method comprises the steps of (a) treating the vegetable protein source with an efficient amount of one or more phytase enzymes; and (b) treating the vegetable protein source with an efficient amount of one or more proteolytic enzymes.

Compared to known method for obtaining protein hydrolysates, the present method improves the availability of the proteins, thereby leading to increased extraction, higher yields and improved protein utilization.

The vegetable protein source subjected to the method of the invention may be any proteinaceous vegetable, in particular a legume, a cereal, a composite plant or a crucifera. Preferably, the legume is selected from the group consisting of soy bean, faba bean, pea, and lupine (*Lupinus albus*), more preferably the legume is soy beans. Preferably, the cereal is selected from the group consisting of wheat, corn, barley, rye, oat, rice, sorghum, sesame (*Sesamum indicum*), and millet (*Panicum miliaceum*). An example of a useful composite plant is sunflower (Helianthus), and an example of a useful crucifera is rape (rape seed, e.g. *Brassica napus*).

The vegetable protein source is preferably soy bean.

The proteinaceous vegetable subjected to the method of the invention may be provided in any form, including "processed forms" wherein the protein content of the dry matter is increased before the protein subjected to the method according to the invention. For instance, soy protein raw material may obtained as soy beans, defatted soy flakes, soy meal, soy concentrate or soy isolate. Such proteinaceous raw material typically contains from about 42% to about 95% protein.

The protein source may be pre-treated in any conventional manner prior to being subjected to the method of the present invention. In particular the protein source may be dried and/or grounded, i.e. processed into meal or flakes (such as soy bean meal or flakes).

The two steps, (a) and (b) of the method of the invention, may be carried out as consecutive steps, or the two steps may be carried out simultaneously.

Also, the vegetable protein source may be treated with one enzyme preparation comprising one or more phytase enzymes and one or more proteolytic enzymes, or the vegetable protein source may be treated with two or more enzyme comprising a one or more phytase enzymes and/or one or more proteolytic enzymes.

It is at present contemplated that the method of the invention is preferably carried out at a pH of the suspension of from about 3 to about 9, more preferably of from about pH 4 to about pH 7.

It is also contemplated that the method of the invention is preferably carried out at a temperature of from about 10° C. to about 70° C., more preferably of from about 35° C. to about 65° C.

In a more specific embodiment, the method comprises the subsequent steps of (i) suspending a vegetable protein source in water;

(ii) proteolytically hydrolysing the protein by subjecting the suspension to enzymatic treatment with one or more phytase enzymes and one or more proteolytic enzyme;

(iii) inactivating the enzymes; and optionally (iv) separating the hydrolysed protein from the suspension.

Inactivation of the enzyme may be carried out by conventional methods for inactivating enzymes, e.g. by heat treatment, i.e. elevating the temperature of the hydrolysis suspension or mixture to a temperature which denatures the enzymes, typically to a temperature of above 85° C.

The separating step may be carried out by conventional methods for separating hydrolysed protein from suspensions, e.g. by centrifugation or membrane filtrating the suspension containing the protein hydrolysate.

In general terms, the method of the invention may be carried out similar to conventional methods for obtaining protein hydrolysates, e.g. as described in U.S. Pat. No. 4,324,805, U.S. Pat. No. 4,100,024 and WO 92/15696, which publications are hereby incorporated by reference.

Phytase Enzymes

The method of the invention for the solubilization of proteins in a vegetable protein source comprises treating the vegetable protein source with an efficient amount of one or more phytase enzymes.

In the context of this invention, a phytase enzyme is an enzyme which catalyzes the removal of inorganic phosphorous from various myoinositol phosphates. Phytase enzymes are preferably derived from a microbial source such as bacteria, fungi and yeasts, but may also be of vegetable origin.

In a preferred embodiment, the phytase enzyme is derived from a fungal strain, in particular a strain of Aspergillus, e.g *Aspergillus niger, Aspergillus oryzae, Aspergillus ficuum, Aspergillus awamori, Aspergillus nidulans* and *Aspergillus terreus*. Most preferred is a phytase enzyme derived from a strain of *Aspergillus niger* or a strain of *Aspergllus oryzae*.

In another preferred embodiment, the phytase enzyme is derived from a bacterial strain, in particular a strain of Bacillus or a strain of Pseudomonas. Preferably the phytase enzyme is derived from a strain of *Bacillus subtilis*.

In yet another preferred embodiment, the phytase enzyme is derived from a yeast, in particular a strain of Kluveromyces or a strain of Saccharomyces. Preferably the phytase enzyme is derived from a strain of *Saccharomyces cerevisiae*.

In the context of this invention "an enzyme derived from" encompasses an enzyme naturally produced by the particular strain, either recovered from that strain or encoded by a DNA sequence isolated from this strain and produced in a host organism transformed with said DNA sequence.

The phytase enzyme may be derived from the microorganism in question by use of any suitable technique. In particular, the phytase enzyme may be obtained by fermentation of a phytase producing microorganism in a suitable nutrient medium, followed by isolation of the enzyme by methods known in the art.

The broth or medium used for culturing may be any conventional medium suitable for growing the host cell in question, and may be composed according to the principles of the prior art. The medium preferably contain carbon and nitrogen sources and other inorganic salts. Suitable media, e.g. minimal or complex media, are available from commercial suppliers, or may be prepared according to published receipts, e.g. the American Type Culture Collection (ATCC) Catalogue of strains.

After cultivation, the phytase enzyme is recovered by conventional method for isolation and purification proteins from a culture broth. Well-known purification procedures include separating the cells from the medium by centrifugation or filtration, precipitating proteinaceous components of the medium by means of a salt such as ammonium sulphate, and chromatographic methods such as e.g. ion exchange chromatography, gel filtration chromatography, affinity chromatography, etc.

Alternatively, the phytase enzyme is preferably produced in larger quantities using recombinant DNA techniques, e.g. as described in EP-A1-0 420 358, which publication is hereby incorporated by reference.

Preferably, a fungus of the species Aspergillus which has been transformed with the phytase-encoding gene obtained from the species *Aspergillus ficuum* or *Aspergillus niger,* is cultured under conditions conducive to the expression of the phytase-encoding gene as described in EP-A1-0 420 358.

The phytase-containing fermentation broth is preferably treated by means of both filtration and ultra-filtration prior to being used in the (formulation) of the present invention.

It is at present contemplated that an amount of phytase efficient for improving the solubility of the vegetable protein corresponds to of from about 2 to about 50000 FYT (as defined below) per kg of vegetable protein source, preferably of from about 50 to about 30000 FYT per kg of vegetable protein source, most preferred of from about 100 to about 10000 FYT per kg of vegetable protein source.

Proteolytic Enzymes

The method of the invention for the solubilization of proteins in a vegetable protein source also comprises treating the vegetable protein source with an efficient amount of one or more proteolytic enzymes.

The proteolytic enzyme may be a microbial enzyme, preferably a protease derived from a bacterial or a fungal strain, or the proteolytic enzyme may be trypsin or pepsin. In a preferred embodiment, the proteolytic enzyme is a bacterial protease derived from a strain of Bacillus, preferably a strain of *Bacillus subtilis* or a strain of *Bacillus licheniformis*. Commercially available Bacillus proteases are Alcalase™ and Neutrase™ (Novo Nordisk A/S, Denmark). In another preferred embodiment, the proteolytic enzyme is a fungal protease derived from a strain of Aspergillus, preferably a strain of *Aspergillus aculeatus,* a strain of *Aspergillus niger,* a strain of *Aspergillus oryzae*. A commercially available Aspergillus protease is Flavourzyme™ (Novo Nordisk A/S, Denmark).

It is at present contemplated that the amount of proteolytic enzyme efficient for improving the solubility of the vegetable protein corresponds to of from about 0.0001 to about 0.5 AU (as defined below) per kg of vegetable protein source, preferably of from about 0.001 to about 0.05 AU per kg of vegetable protein source, more preferred of from about 0.005 to about 0.03 AU per kg of vegetable protein source.

Additional Enzymes

As described above, the present invention provides a method for the solubilization of proteins in a vegetable protein source, which method comprises the steps of (a) treating the vegetable protein source with an efficient amount of one or more phytase enzymes; and (b) treating the vegetable protein source with an efficient amount of one or more proteolytic enzymes.

The two steps, (a) and (b) of the method of the invention, may be carried out as consecutive steps, or the two steps may be carried out simultaneously.

In a preferred embodiment, the method of the invention further comprises the step of (c) treating the vegetable protein source with an efficient amount of one or more enzymes selected from the group consisting of lipolytic enzymes and glucosidase enzymes.

The three steps, (a), (b) and (c) of the method of the invention, may be carried out as consecutive steps, or the three steps may be carried out simultaneously. Or the two steps, (a) and (b) of the method of the invention, may be carried out simultaneous, followed by step (c).

The lipolytic enzyme of step (c) may be any triacylglycerol lipase (EC 3.1.1.3).

The glycosidase enzyme of step (c) may be any glycosidase enzyme (EC 3.2, also known as carbohydrases). Preferably, the glycosidase enzyme is an amylase, in particular an α-amylase or a β-amylase, a cellulase, in particular an endo-1,4-β-glucanase (EC 3.2.1.4) or an endo-1,3-β-glucanase (3.2.1.6), a xylanase, in particular an endo-1,4-β-glucanase (EC 3.2.1.8) or a xylan-endo-1,3-β-xylosidase (EC 3.2.1.32), an α-galactosidase (EC 3.2.1.22), a polygalacturonase (EC 3.2.1.15, also known as pectinases), a cellulose-1,4-β-cellobiosidase (EC 3.2.1.91, also known as cellobiohydrolases), an endoglucanase, in particular an endo-1,6-σ-glucanase (EC 3.2.1.75), an endo-1,2-β-glucanase (EC 3.2.1.71), an endo-1,3-β-glucanase (EC 3.2.1.39) or an endo-1,3-α-glucanase (EC 3.2.1.59).

In a more preferred embodiment, the glucosidase enzyme is a polygalacturonase (EC 3.2.1.15), a cellulose-1,4-β-cellobiosidase (EC 3.2.1.91), or an endoglucanase, preferably an endo-1,6-β-glucanase (EC 3.2.1.75), an endo-1,2-β-glucanase (EC 3.2.1.71), an endo-1,3-β-glucanase (EC 3.2.1.39) or an endo-1,3-α-glucanase (EC 3.2.1.59).

Industrial Applications

The method of the invention for the solubilization of proteins in a vegetable protein source, may find application in various industries. In particular the method of the invention find application for the preparation of protein hydrolysates useful as nutrients, e.g. as nutritional additives to foods and beverages.

Therefore, in another aspect, the present invention also provides a protein hydrolysate obtained from a vegetable protein source by the method of the invention.

The protein hydrolysate of the invention may be added to foods or beverages, thereby increasing the nutritional value.

In particular the protein hydrolysate of the invention may be added to animal feed, e.g. feedstuffs for monogastric animals.

Animal Feed Additives

The present invention provides an animal feed additive comprising one or more phytase enzymes and one or more proteolytic enzymes.

When added to animal feed, the combination of one or more phytase enzymes and one or more proteolytic enzymes improves the availability of the proteins present in animal feed of vegetable origin, thereby leading to increased extraction of the vegetable proteins, higher protein yields and improved protein utilization. Thereby, the nitrogen digestibility and the nutritive value of the fodder becomes increased, and the growth rate and/or feed conversion ratio (i.e. the weight of ingested feed relative to weight gain) of the animal is improved.

In the context of this invention, an animal feed additive is an enzyme preparation comprising one or more phytase enzymes and one or more proteolytic enzymes and suitable carriers and/or excipients, and which enzyme preparation is provided in a form that is suitable for being added to animal feed. The animal feed additive of the invention may be prepared in accordance with methods known in the art and may be in the form of a dry or a liquid preparation. The enzyme to be included in the preparation, may optionally be stabilized in accordance with methods known in the art.

In a specific embodiment the animal feed additive of the invention is a granulated enzyme product which may readily be mixed with feed components, or more preferably, form a component of a pre-mix. The granulated enzyme product may be coated or uncoated. The particle size of the enzyme granulates preferably is compatible with that of feed and pre-mix components. This provides a safe and convenient mean of incorporating the enzymes into feeds.

In another specific embodiment, the animal feed additive of the invention is a stabilized liquid composition, which may be an aqueous or oil-based slurry.

In yet another specific embodiment, one or more of the enzymes are applied before or after pelleting or extrusion of the feed.

The animal feed additive of the invention may exert its effect either in vitro (by modifying components of the feed) or in vivo. The feed additive of the invention is particularly suited for addition to animal feed compositions containing high amounts of proteinaceous vegetables, in particular legumes, cereals, composite plants or crucifera. Preferably, the legume is soy bean, faba bean, pea, and/or lupine (*Lupinus albus*). Most preferably the legume is soy beans. Preferably, the cereal is wheat, corn, barley, rye, oat, rice, sorghum, sesame (*Sesamum indicum*), and millet (*Panicum miliaceum*). An example of a composite plant is sunflower (Helianthus), and an example of a useful crucifera is rape (rape seed, e.g. *Brassica napus*).

In another preferred embodiment, the invention provides an animal feed additive which comprises one or more additional enzymes selected from the group consisting of lipolytic enzymes and glucosidase enzymes.

The lipolytic enzyme may be any triacylglycerol lipase (EC 3.1.1.3).

The glycosidase enzyme may be any glycosidase enzyme (EC 3.2, also known as carbohydrases). Preferably, the glycosidase enzyme is an amylase, in particular an α-amylase or a β-amylase, a cellulase, in particular an endo-1,4-β-glucanase (EC 3.2.1.4) or an endo-1,3-β-glucanase (3.2.1.6), a xylanase, in particular an endo-1,4-β-glucanase (EC 3.2.1.8) or a xylan-endo-1,3-β-xylosidase (EC 3.2.1.32), an α-galactosidase (EC 3.2.1.22), a polygalacturonase (EC 3.2.1.15, also known as pectinases), a cellulose-1,4-β-cellobiosidase (EC 3.2.1.91, also known as cellobiohydrolases), an endoglucanase, in particular an endo-1,6-σ-glucanase (EC 3.2.1.75), an endo-1,2-β-glucanase (EC 3.2.1.71), an endo-1,3-β-glucanase (EC 3.2.1.39) or an endo-1,3-α-glucanase (EC 3.2.1.59).

In a more preferred embodiment, the glucosidase enzyme is a polygalacturonase (EC 3.2.1.15), a cellulose-1,4-β-cellobiosidase (EC 3.2.1.91), or an endoglucanase, preferably an endo-1,6-β-glucanase (EC 3.2.1.75), an endo-1,2-β-glucanase (EC 3.2.1.71), an endo-1,3-β-glucanase (EC 3.2.1.39) or an endo-1,3-α-glucanase (EC 3.2.1.59).

It is at present contemplated that the pH of the animal feed additive should be in the range of from about pH 2 to about pH 8.

It is at present contemplated that the amount of phytase activity in the animal feed additive should be in the range of from about 200 to about 50000 FYT (as defined below) per gram of the total composition, preferably in the range of from about 500 to about 10000 FYT per gram of the total composition, most preferred in the range of from about 2000 to about 6000 FYT per gram of the total composition.

Preferably, the amount of additive added to the animal feed should be sufficient to provide a feed composition containing at least 50 FYT per kg feed, more preferably, between about 100 and about 2000 FYT per kg feed.

It is to be understood that the actual amount of Phytase Units which should be added to the feed in order to enhance the nutritive value, i.e. the nitrogen digestibility, will depend on the composition of the feed itself. Feedstuffs containing high amounts of phytic acid will generally require the addition of higher amounts of phytase activity. The necessary amount of phytase may easily by determined by the skilled person.

Phytase Activity (FYT)

The phytase activity may be determined using sodium phytate as substrate. When subjected to the action of phytase, inorganic phosphorous is liberated from sodium phytate. In a ferrous/molybdenum containing reagent, phosphorous ($PO_4$) forms a complex, which can be monitored spectrophotometrically at 750 nm.

One Phytase Unit (FYT) is defined as the amount of enzyme which under standard conditions (i.e. at pH 5.5, 37° C., a substrate concentration of 5.0 mM sodium phytate, and a reaction time of 30 minutes) liberates 1 μmol of phosphate per minute.

A standard operating procedure EAL-SM-0403.01 describing this analytical method in more detail is available upon request to Novo Nordisk A/S, Denmark, which publication is hereby included by reference.

Protease Activity (AU)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU) is defined as the amount of enzyme which under standard conditions (i.e. 25° C., pH 7.5 and 10 min. reaction time) digests hemoglobin at an initial rate such that there is liberated per minute an amount of TCA soluble product which gives the same color with phenol reagent as one milliequivalent of tyrosine.

A folder AF 4/5 describing the analytical method in more detail is available upon request to Novo Nordisk A/S, Denmark, which folder is hereby included by reference.

EXAMPLES

The invention is further illustrated with reference to the following examples which are not intended to be in any way limiting to the scope of the invention as claimed.

Example 1

Soy Protein Hydrolysis

Soy protein concentrate (Unico 75, Loders Crooklaan, NL) was suspended in deionized water at 50° C.

The mixture was heat treated at 85° C. for 3 minutes and cooled to 55° C., the temperature of hydrolysis. pH was adjusted to 8.5 using 4 N NaOH.

The mixture was divided into three vessels for three comparative experiments:

1) Hydrolysing with:
   Alcalase™ 2.4 L, dosage 2 w/w % of protein content.
   Neutrase™ 0.5 L, dosage 1 w/w % of protein content.
   Phytase Novo™ (an Aspergillus phytase, 6900 FYT/g), dosage 1 mg/g soy concentrate. pH adjusted to 4.5 with HCl. Phytase is added when pH<6.6.

2) Hydrolysing with:
   Alcalase™ 2.4 L, dosage 2 w/w % of protein content.
   Neutrase™ 0.5 L, dosage 1 w/w % of protein content.

3) pH was adjusted to 6.2 using HCl. Phytase Novo™ (an Aspergillus phytase, 6900 FYT/g), dosage 1 mg/g soy concentrate.

The three hydrolyses were followed by monitoring the degree of hydrolysis and the osmolality. The results are presented in Tables 1–2, below.

TABLE 1

| | Osmolality, mOsm/kg. | | |
|---|---|---|---|
| Time (minutes) | Exp. 1) | Exp. 2) | Exp. 3) |
| 0 | 103 | 102 | 103 |
| 15 | 200 | 173 | 145 |
| 35 | 211 | 183 | 147 |
| 65 | 232 | 201 | 139 |
| 125 | 241 | 208 | 142 |
| 185 | 250 | 221 | 140 |

TABLE 2

| | Degree of Hydrolysis, % DH | | |
|---|---|---|---|
| Time (minutes) | Exp. 1) | Exp. 2) | Exp. 3) |
| 20 | 12.2 | 11.9 | −1.9 |
| 40 | 13.9 | 12.6 | −1.6 |
| 70 | 13.2 | 12.8 | −2.0 |
| 130 | 17.3 | 15.0 | −2.6 |
| 190 | 19.5 | 18.2 | −2.4 |

Both measurements of the degree of hydrolysis (%DH) show an increased degradation of the substrate. Experiment 1 yielded more solubilized protein (78.8%) when compared to Experiment 2 (77.3%).

Example 2

In Vitro N-digestibility of Soy Bean Meal

Two samples were prepared:

Sample A: 1 g of soybean meal

Sample B: 1 g of soybean meal with addition of 0.032 g Phytase Novo™ (an Aspergillus phytase, 5000 FYT/g)

Each sample was incubated with pepsin at pH 2.4 for 2 hours followed by incubation with pancreatin at pH 6.8 for 16 hours. Suspended but not digested protein was precipitated with sulfosalicylic acid. The undigested protein (as well as other undigested components) was collected by filtration and drying. The dry matter of the filter cake and of the sample was determined, and the amount of nitrogen (N) was determined by the Kjeldahl method.

The N digestibility was calculated as follows:

$$\frac{N_{sample} * Dry\ matter_{sample} - N_{filtercake} * dry\ matter_{filtercake}}{N_{sample} * Dry\ matter_{sample}} * 100$$

The protein digestibility was calculated by multiplying the nitrogen (N) digestibility by 6.25.

The following protein digestibility results were obtained:
Sample A (without phytase): 88.4%
Sample B (with phytase): 89.9%

Example 3
Effect of Phytase on Apparent Nitrogen Digestibility and Nitrogen Utilization in Pigs Balance trials on pigs (weight 46–52 kg) on a barley-wheat-soy diet.

Diet composition:
Barley 50.8%
Wheat 20.0%
Soy 24.0%
Animal fat 2.0%
Melasse 1.0%
Minerals, vitamins and amino acids 2.2%

No addition of inorganic phosphate to the diet. The diet was pelletized at a temperature of above 60° C.

Balance trial was conducted with an adaption period of 5 days and a 7 days collection period.

12 pigs were divided into two groups. The first group was fed the diet and the second group was fed the same diet but with addition of 20.3 g/100 kg feed of Phytase Novo™ (an Aspergillus phytase, 7370 FYT/g).

The content of nitrogen in the diet, faeces and urine was measured and the apparent nitrogen digestibility and nitrogen utilization was calculated.

The results are presented in Table 3, below.

TABLE 3

Nitrogen Digestibility and Nitrogen Utilization

| Nitrogen (g/day) | Diet without Phytase | Diet with Phytase | S.E.M. |
| --- | --- | --- | --- |
| Consumed | 44.5 | 44.5 | |
| Faeces | 6.8 | 6.2 | 0.1* |
| Urine | 20.3 | 19.5 | 0.8 NS |
| Deposit | 17.4 | 18.7 | 0.6 NS |
| Digested | 37.6 | 38.3 | 0.1* |
| Digested, % | 84.7 | 86.1 | 0.3* |

*p ≦ 0.01
NS (not significant): p > 0, 05
S.E.M.: standard error mean

We claim:

1. An animal feed additive comprising one or more phytases and one or more bacterial proteolytic enzymes.

2. The animal feed additive of claim 1, further comprising one or more additional enzymes selected from the group consisting of lipolytic enzymes and glucosidase enzymes.

3. The animal feed additive of claim 2, in which the glucosidase enzyme is selected from the group consisting of a carbohydrase, amylase, cellulase, xylanase, α-galactosidase, polygalacturonase, and cellobiohydrolase.

4. The animal feed additive of claim 2, in which the glucosidase enzyme is a polygalacturonase, cellulose-1,4-β-cellobiosidase, or endoglucanase.

5. The animal feed additive of claim 1, wherein the phytase is a vegetable phytase, fungal phytase, bacterial phytase, or phytase obtained from a yeast.

6. The animal feed additive of claim 5, wherein the phytase is a fungal phytase derived from a strain of Aspergillus.

7. The animal feed additive of claim 5, wherein the phytase is a bacterial phytase derived from a strain of Bacillus or Pseudomonas.

8. The animal feed additive of claim 5, wherein the phytase is derived from Kluveromyces or Saccharomnyces.

9. The animal feed additive of claim 1, wherein the protease is derived from a strain of Bacillus.

10. An animal feed comprising one or more feed components, one or more phytases and one or more bacterial proteolytic enzymes.

11. The animal feed of claim 10, further comprising one or more additional enzymes selected from the group consisting of lipolytic enzymes and glucosidase enzymes.

12. The animal feed of claim 11, in which the glucosidase enzyme is selected from the group consisting of a carbohydrase, amylase, cellulase, xylanase, α-galactosidase, polygalacturonase, and cellobiohydrolase.

13. The animal feed of claim 11, in which the glucosidase enzyme is a polygalacturonase, cellulose-1,4-β-cellobiosidase, or endoglucanase.

14. An animal feed comprising a protein hydrolyzate obtained by treating a vegetable protein source with one or more phytases and one or more bacterial proteolytic enzymes.

15. A method solubilizing proteins in a vegetable protein source, which method comprises the steps of (a) treating the vegetable protein source with an efficient amount of one or more phytase enzymes;

(b) treating the vegetable protein source with an efficient amount of one or more bacterial proteolytic enzymes; and (c) treating the vegetable protein source with an efficient amount of one or more lipolytic enzymes and/or one or more glucosidase enzymes.

16. The method of claim 15, in which the glucosidase enzyme is selected from the group consisting of a carbohydrase, amylase, cellulase, xylanase, α-galactosidase, polygalacturonase, and cellobiohydrolase.

17. The method of claim 16, in which the glucosidase enzyme is a polygalacturonase, cellulose-1,4-β-cellobiosidase, or endoglucanase.

18. The method of claim 15, wherein steps (a), (b) and (c) are carried out simultaneously.

19. The method of claim 15, wherein the phytase is a vegetable phytase, fungal phytase, bacterial phytase or phytase derived from a yeast.

20. The method of claim 19, wherein the phytase is a fungal phytase derived from a strain of Aspergillus.

21. The method of claim 19, wherein the phytase is a bacterial phytase derived from a strain of Bacillus or Pseudomonas.

22. The method of claim 19, wherein the phytase is derived from Kluveromyces or Saccharomyces.

23. The method of claim 15, wherein the protease is derived from a strain of Bacillus.

24. The method of claim 15, wherein the vegetable protein source is a legume, composite plant, crucifera, cereal, or a mixture thereof.

25. The method of claim 15, wherein the vegetable protein source is soy bean.

26. The method of claim 15, wherein the enzymatic treatment is carried out at a pH of from 3 to 9.

27. The method of claim 15, wherein the enzymatic treatment is carried out at a temperature of from about 10 to about 70° C.

28. A method of producing a protein hydrolyzate, comprising
   (a) treating a vegetable protein source with an efficient amount of one or more phytase enzymes;
   (b) treating the vegetable protein source with an efficient amount of one or more bacterial proteolytic enzymes; and
   (c) treating the vegetable protein source with an efficient amount of one or more lipolytic enzymes and/or one or more glucosidase enzymes.

29. The method of claim 28, in which the glucosidase enzyme is selected from the group consisting of a carbohydrase, amylase, cellulase, xylanase, $\alpha$-galactosidase, polygalacturonase, and cellobiohydrolase.

30. The method of claim 29, in which the glucosidase enzyme is a polygalacturonase, cellulose-1,4-$\beta$-cellobiosidase, or endoglucanase.

31. Amethod of increasing nitrogen digestibility and the nutritive value of food or improving the growth rate and feed conversion ratio of an animal, comprising feeding the animal with an animal feed of claim 10.

* * * * *

UNITED STATES PATENT AND TRADEMARK OFFICE
CERTIFICATE OF CORRECTION

PATENT NO.    :    5,989,600

DATED         :    November 23, 1999

INVENTOR(S)   :    Nielsen et al.

It is certified that error appears in the above-identified patent and that said Letters Patent is hereby corrected as shown below:

In the claims:

Column 10, line 5, delete "Saccharomnyces", insert --Saccharomyces--

Signed and Sealed this

Second Day of January, 2001

Attest:

Attesting Officer

Q. TODD DICKINSON
Commissioner of Patents and Trademarks